(12) United States Patent
Reutter et al.

(10) Patent No.: US 11,526,207 B2
(45) Date of Patent: Dec. 13, 2022

(54) TRACKER FOR A HEAD-MOUNTED DISPLAY

(71) Applicant: Scopis GmbH, Berlin (DE)

(72) Inventors: Andreas Reutter, Berlin (DE); Christopher Özbek, Berlin (DE)

(73) Assignee: Stryker European Operations Limited, Carrigtwohill (IE)

( * ) Notice: Subject to any disclaimer, the term of this patent is extended or adjusted under 35 U.S.C. 154(b) by 107 days.

(21) Appl. No.: 16/904,634

(22) Filed: Jun. 18, 2020

(65) Prior Publication Data
US 2021/0004079 A1     Jan. 7, 2021

(30) Foreign Application Priority Data

Jul. 4, 2019  (EP) ..................................... 19184373

(51) Int. Cl.
| G09G 5/00 | (2006.01) |
| G06F 3/01 | (2006.01) |
| A61B 34/20 | (2016.01) |
| A61B 90/00 | (2016.01) |
| G02B 27/01 | (2006.01) |

(52) U.S. Cl.
CPC .............. G06F 3/012 (2013.01); A61B 34/20 (2016.02); A61B 90/37 (2016.02); G02B 27/0176 (2013.01); *A61B 2034/2055* (2016.02); *A61B 2034/2074* (2016.02);
(Continued)

(58) Field of Classification Search
CPC  A61B 2017/00477; A61B 2017/00876; A61B 2034/107; A61B 2034/2055; A61B 2034/2074; A61B 2090/365; A61B 2090/372; A61B 2090/373; A61B 2090/3937; A61B 2090/3983; A61B 2090/502; A61B 34/20; A61B 90/37; A61B 90/39; G02B 27/0176; G06F 3/012
See application file for complete search history.

(56) References Cited

U.S. PATENT DOCUMENTS

| 2003/0185434 | A1* | 10/2003 | Lee .......................... G06F 3/012 |
| | | | 382/154 |
| 2014/0152550 | A1 | 6/2014 | Beall et al. |

(Continued)

FOREIGN PATENT DOCUMENTS

| WO | 2018203304 A1 | 11/2018 |
| WO | 2019037605 A1 | 2/2019 |

OTHER PUBLICATIONS

ART GmbH, "System User Manual", Apr. 1, 2015, https://www.schneider-digital.com/support/download/Tools_Ressourcen/ART_Tracking/Dokumentation/SMARTTRACK_User_Manual_2.11.pdf, pp. 1-138.

(Continued)

*Primary Examiner* — Insa Sadio
(74) *Attorney, Agent, or Firm* — Howard & Howard Attorneys PLLC (57) ABSTRACT

A tracker 30 for a Head-Mounted Display, HMD, unit is provided. The tracker 30 comprises a carrier element 10 carrying one or more markers 16*a*, 16*b* that are configured to permit determining a position of the tracker 30. The carrier element 10 comprises at least one magnetic element 32 configured to cooperate with at least one magnetic element 22 provided on the HMD unit 62, or on a base element 20 that is to be fixed to the HMD unit 62, for detachably attaching the carrier element 10 to the HMD unit 62.

12 Claims, 7 Drawing Sheets

(52) U.S. Cl.
CPC ... *A61B 2090/365* (2016.02); *A61B 2090/372* (2016.02); *A61B 2090/373* (2016.02)

(56) References Cited

U.S. PATENT DOCUMENTS

| | | |
|---|---|---|
| 2017/0351098 A1 | 12/2017 | Osterhout et al. |
| 2018/0108179 A1 | 4/2018 | Tomlin et al. |
| 2018/0185100 A1 | 7/2018 | Weinstein et al. |
| 2019/0057537 A1* | 2/2019 | Ohba .................. G06T 15/04 |
| 2019/0087021 A1* | 3/2019 | Balan .................. G06T 19/006 |
| 2019/0138053 A1* | 5/2019 | Hwang ................ G02B 27/01 |

OTHER PUBLICATIONS

Mohr, Peter et al., "TrackCap: Enabling SmartPhones for 3D Interaction on Mobile Head-Mounted Displays", Human Factors in Computing Systems, ACM, May 4-9, 2019, pp. 1-11.
English language abstract and machine-assisted English translation for WO 2019037605 extracted from espacenet.com database on Jul. 16, 2020, 10 pages.

* cited by examiner

TRACKER FOR A HEAD-MOUNTED DISPLAY

CROSS-REFERENCE TO RELATED APPLICATIONS

This application claims priority to European Patent Application No. EP19184373, filed on Jul. 4, 2019, the entire contents of which are hereby incorporated by reference.

TECHNICAL FIELD

The present disclosure generally relates to a tracker for a Head-Mounted Display (HMD). In particular, a tracker which is configured to be detachably attachable to a HMD is presented.

BACKGROUND

Trackers are attached, for example, to surgical tools for determining the position of the respective surgical tool. The tracked surgical tool may be part of a surgical navigation system, which helps the surgeon navigate the tool by providing visual or acoustic guidance to the surgeon. Commonly, in such a surgical navigation system, the patient is tracked also, which enables calculating the position of the surgical tool relative to the patient.

The trackers may be passive or active trackers. A passive tracker comprises markers that reflect light. The reflected light can be detected by a camera of the surgical navigation system. An active tracker generates light (e.g., via a light-emitting diode) that can be detected by the camera.

For reliably determining the position of a passive tracker, and, therefore, of the tool to which the tracker is attached, it is important that the reflective surface is not contaminated, for example by blood, and is not damaged, for example by scratches. The reflective surface may be provided by a retroreflective material, for example a retroreflective foil, which is characterised by good reflection properties. A possible material for the markers is also glass, which is easier to clean than a retroreflective surface but has lower reflection properties than a retroreflective surface.

For enabling a reliable determination of the position of the tracker also after a plurality of surgical cycles, it is common to replace the markers or, alternatively, to provide a highly redundant number of markers so that damages and contaminations have no effect on the accuracy of the determined position and that the markers need to be replaced only occasionally. When replacing the markers, it is decisive to reproduce the positional accuracy, that means, the new marker should be at exactly the same position as the replaced marker was before.

It is further known that a surgeon wears an HMD during surgery, which allows visualization of information such as instructions, warnings or other features relevant for the surgeon. US 2018/0185100 A1 teaches tracking the position of such an HMD during surgery so as to visualize virtual images overlaid on the real world environment.

SUMMARY

There is a need for a solution that permits a reliable use of a tracked HMD.

According to a first aspect, a tracker for an HMD unit is provided. The tracker comprises a carrier element carrying one or more markers that are configured to permit determining a position of the tracker, wherein the carrier element is configured to be detachably attachable to the HMD unit. In particular, the carrier element comprises at least one magnetic element configured to cooperate with at least one magnetic element provided on the HMD unit, or on a base element to be fixed to the HMD unit, for detachably attaching the carrier element to the HMD unit.

The HMD unit may comprise a head-mountable structure, which may comprise an adjustable headband for holding the HMD unit on a user's head. The HMD may comprise a display configured to be arranged in front of the user's face. The display may be configured such that virtual information, including virtual images, can be displayed at desired coordinates in a desired coordinate system. In this manner, the virtual information can be overlaid onto real world images seen through the HMD unit at desired coordinates in the real world environment.

The virtual information may be, for example, patient image data, surgical planning objects such as tumors, trajectories, points, lines, implants etc., alignment information, tool information, text notes, picture notes (e.g., one or more icons), one or more video windows, status information, warning information, etc. The displayed virtual information may be overlaid on real world environment such as the real patient anatomy seen through the HMD unit.

At least some of the one or more markers may be or may include passive markers. Thus, they may be reflective to light (e.g., of a predetermined light spectrum, such as infrared light). Based on the reflected light, a position of the tracker and thus of the HMD unit can be determined by a navigation system.

The one or more markers are provided on, at or in the carrier element such that it or they can be detected by the navigation system. The carrier element is so shaped and sized that it can be detachably attached to the HMD unit. Thus, for example, the carrier element may have a curved shape that is adapted to a curved shape of the HMD unit.

The tracker may comprise only one marker, or it may comprise two, three, four or more markers. Generally, it may comprise any number of markers. In case more than two markers are provided at the carrier element, the position and orientation of the tracker can be determined accurately and reliably by way of the more than two markers. If only one marker is provided or if only two markers are provided at the carrier element, at least one further source of information may be provided that compensates for the "missing" tracker(s). The at least one further source of information may comprise one or more of an inertial measurement unit (IMU) or a tracking system of the HMD, by means of which the position and the orientation of the tracker may be determined in combination with detection of the one or more markers at the carrier element. Such other information may be synchronized or averaged using several measurements over time.

The at least on magnetic element of the carrier element and the at least one magnetic element of the HMD unit or the base element are configured and arranged so as to detachably attach the carrier element, optionally via the base element, to the HMD unit. Thus, the magnetic elements may be positioned so as to contact each other or so as to be in close proximity to each other when the carrier element is attached to the HMD unit, optionally via the base element. Further, the magnetic elements on the carrier element and the HMD unit or on the base element are so oriented that the magnetic elements attract each other and form a magnetic connector. Due to the magnetic elements, the carrier element can be clipped on the HMD unit, or on the base element that fixed to the HMD unit, in a simple and reliable manner.

In one variant, two or more markers are provided, wherein at least some of the two or more markers may be arranged along a longitudinal extension of the carrier element, and the carrier element may have a curved shape in its longitudinal extension. In the case of three or more markers, at least half of the markers may be arranged so as to be spaced apart from each other in the longitudinal extension. The curved shape of the carrier element may be adapted to a curved shape of the HMD unit, so that the carrier element may be integrated into the HMD unit so as to ensure a comfortable wearing. Furthermore, since the two or more markers may be arranged along the curved shape, the two or more markers may capture and reflect light of a large spatial angle, thereby enhancing accuracy of position determination. The curved shape of the carrier element, and of the HMD unit, may substantially correspond to the curvature of a person's head.

In a further variant, the carrier element may have an alignment element configured to cooperate with a corresponding alignment element provided on the HMD unit. By way of the alignment elements, the carrier element may be accurately positionally aligned with respect to the HMD unit. Thus, if the carrier element is replaced with a new carrier element having, for example, clean and/or undamaged markers, the new carrier element may be accurately positioned with respect to the HMD unit in a reliable and simple manner.

In another variant, the tracker may comprise the base element configured to be fixed to the HMD unit so as to extend in a circumferential direction of the HMD unit when being fixed to the HMD unit. In this variant, the carrier element and the base element may each comprise the respective at least one magnetic element for detachably attaching the carrier element via the base element to the HMD unit. The HMD unit may be, for example, a HMD unit commonly available on the market which is subsequently equipped with the base element comprising the at least one magnetic element. Thus, the carrier element is detachably attachable to the base element in a simple and fast manner by plugging the carrier element on the base element.

In an aspect of the other variant, the carrier element and the base element each comprise an alignment element configured to cooperate with each other so as to positionally align the carrier element with the base element. In this aspect of the other variant, the carrier element may be accurately aligned with respect to the HMD unit by way of the alignment element provided on the base element cooperating with the alignment element of the carrier element. Thus, if the carrier element is replaced with a new carrier element having, for example, clean and/or undamaged one or more markers, the new carrier element may be accurately positioned with respect to the HMD unit in a reliable and simple manner. In a variant without base element, both the carrier element and the HMD unit may each comprise an alignment element configured to cooperate with each other so as to positionally align the carrier element with the HMD unit.

The base element and the carrier element may comprise complementary form-fitting alignment elements. The form-fitting alignment elements may engage with each other, thereby positionally aligning the base element and the carrier element with each other. The complementary form-fitting elements provide a simple and reliable solution for reproducibly aligning the position of the base element and the position of the carrier element. In a variant without base element, both the carrier element and the HMD unit may comprise complementary form-fitting alignment elements. The form-fitting alignment elements may engage with each other, thereby positionally aligning the HMD unit and the carrier element with each other.

The base element may be configured for being permanently fixed to the HMD unit. The base element may be, for example, glued or screwed to the HMD unit. Alternatively, the base element is also detachably fixed to the HMD unit, for example, by a clip-on mechanism and/or a magnetic connection. In such variants, a force required to detach the carrier element from the HMD unit may be significantly higher than a force required to details the carrier element from the base element.

According to an aspect, two or more markers are provided which may at least include one or more passive flat-shaped markers and one or more passive sphere-shaped markers. Thus, the carrier element carries both at least one passive flat-shaped marker and at least one passive sphere-shaped marker. Sphere-shaped markers have the advantage that they can see light that is incident from substantially all directions, whereas flat-shaped markers only see light under incident angles up to about 45°. On the other hand, flat-shaped markers are, compared to sphere-shaped markers, more cost-effective, easier to clean and simpler to produce. Furthermore, flat-shaped markers which are arranged adjacent to each other do not cover each other, i.e., they do not obstruct the line of view in regard of an adjacent marker. Thus, providing both at least one passive flat-shaped marker and at least one passive sphere-shaped marker allows combining the characteristics and advantages of both marker types.

In an example of this aspect, the one or more sphere-shaped markers are arranged in a central region of the carrier element with respect to a longitudinal extension of the carrier element, and the one or more flat-shaped markers are arranged laterally to the one or more sphere-shaped markers. Thus, in this example, the centrally arranged sphere-shaped marker or markers may reflect incoming light (e.g., from both sides and from the front), and the laterally arranged flat-shaped marker or markers may also reflect incoming light (e.g., from one side and from the front), but without covering the sphere-shaped marker or markers. In some implementations, one, to or more flat-shaped markers are arranged on both the first side of the one or more sphere-shaped markers and on second side opposite to the first side.

According to a further aspect, the tracker may comprise one or more verification elements configured to permit verifying that the carrier element and the HMD unit are positionally aligned with each other. By means of the one or more verification elements, a correct alignment of the carrier element and the HMD unit (optionally via the base element, if present) may be ascertained in a simple manner. For example, the one or more verification elements may be configured so as to allow an visual check whether the carrier element and the base element fixedly attached to the HMD unit are correctly aligned with respect to each other.

The verification elements may have different configurations. According to one configuration, markings may be provided on the carrier element and the base element so as to align with each other when the base element and the carrier element are positionally aligned. The markings may be, for example, lines or dots that coincide when the carrier element and the base element are correctly aligned. According to another configuration, a gap may be formed between the base element and the carrier element, and the size of the gap may be constant over the whole length of the gap when the base element and the carrier element are positionally aligned. According to a further another configuration, a window may be provided on the carrier element so as to align with a marking on the base element when the base element and the carrier element are positionally aligned. Accordingly, the marking can be seen through the window in case of correct alignment. The marking may be, for example, a geometrical pattern, text information, letters and/or picture information.

In a second aspect, an HMD for a surgical navigation system is provided. The HMD comprises an HMD unit and a tracker comprising one or more markers that are configured to permit determining a position of the tracker, wherein the tracker is detachably attached to the HMD unit. The HMD unit and the tracker may be configured as described above, or otherwise.

The tracker is detachably attached to the HMD unit, thereby allowing a replacement of the one or more markers by simply replacing the tracker carrying the one or more markers. The tracker may be, for example, detachably attached to a front side of the HMD unit. The front side may be a display-carrying side of the HMD unit.

In a variant of the second aspect, the tracker may comprise carrier element that is carrying the one or more markers and that is detachably attached to the HMD unit or to a base element fixed to the HMD unit, so as to extend in a circumferential direction of the HMD unit. The circumferential direction of the HMD unit may correspond to a longitudinal extension of the carrier element, along which at least some of the one or more markers are arranged. For example, in the case of two or more markers, the placement of the two or more markers along the circumferential direction of the HMD unit allows the two or more markers to receive light incident from the front side of the HMD unit and from left and right sides relative to the front side.

As explained above, the base element may be a separate element fixed to the HMD unit. The HMD unit may be, for example, a HMD unit available on the market which is subsequently equipped ("retro-fitted") with the base element.

The carrier element may comprises a structural interface that is configured to cooperate with a structural interface of the base element or the HMD unit so as to detachably plug the carrier element on the base element or HMD unit. The structural interfaces of the carrier element and the base element or HMD unit may be configured so that, upon cooperation of the structural interfaces, the carrier element is detachably fixed to the base element or the HMD. The structural interfaces may, for example, comprise engaging structures that engage with each other for securing the carrier element to the base element and that can be disengaged from each other for detaching the carrier element from the base element. The engaging structures may, for example, include or be a latching mechanism. The structural interfaces may, for example, include a plurality of dowel joints.

Furthermore, in this variant according to the second aspect, the carrier element and the base element or HMD unit may each comprise at least one magnetic element arranged and configured to cooperate with each other. The at least one magnetic element of the carrier element and the at least one magnetic element of the base element or HMD unit are provided for detachably attaching the carrier element to the base element or HMD unit. Thus, the magnetic elements may be positioned so as to contact each other or as to be in close proximity to each other when the carrier element is attached to the base element or HMD unit. Further, magnetic elements on the different HMD components are so oriented that the magnetic elements attract each other and act as a magnetic connector.

Each of the carrier element and the base element may have a curved shape adapted to a curved shape of the HMD unit. In the case of two or more markers, the two or more markers may be arranged along the curved shape of the carrier element. The placement of the two or more markers along the curved shape of the HMD unit allows the two or more markers to receive light incident from the front side of the HMD unit and from both sides of the HMD unit over a large spatial angle.

In addition, the HMD according to the second aspect or any variant thereof may comprise the alignment elements and/or verification elements as described above with respect to the tracker for a HMD unit.

In a third aspect, a navigation system is provided which comprises an HMD according to the second aspect or any variant thereof and an optical sensor capable of detecting light reflected by the markers and of generating a sensor signal indicative of the detected light.

In a variant of the third aspect, the navigation system may comprise a navigation controller capable of receiving the sensor signal and determining at least one of a position and/or an orientation of the tracker in a coordinate system of the navigation system.

The navigation system may be a surgical or a non-surgical navigation system.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1A:
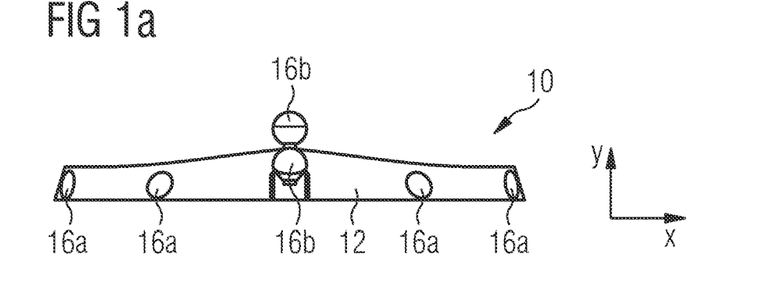
FIGS. 1a-1d schematically show different views of a carrier element of a tracker according to an embodiment of the present disclosure.
Figure 1B:
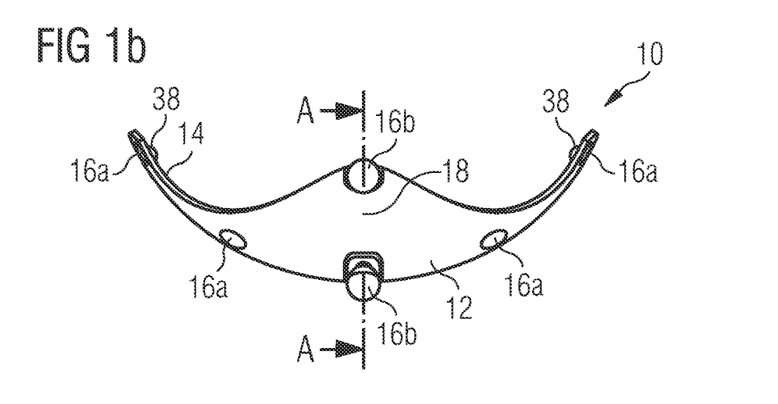
Figure 1C:
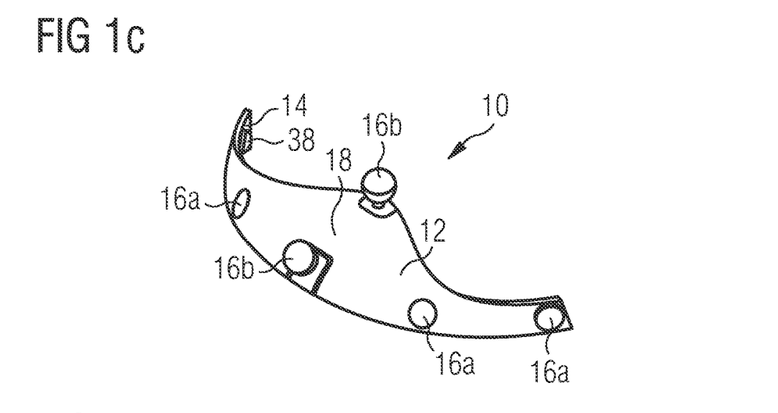
Figure 1D:
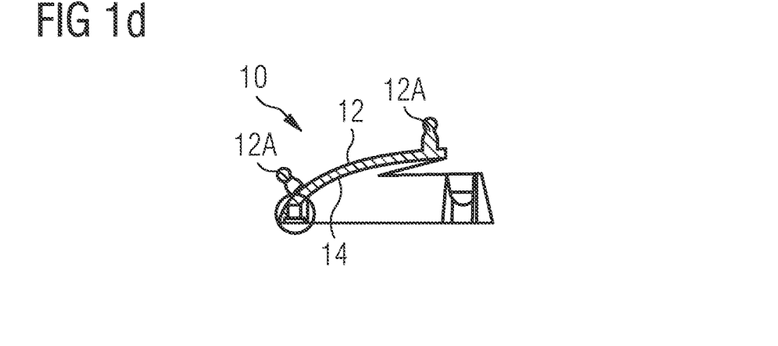

FIGS. 1a to 1d show a carrier element 10 of a tracker according to the present disclosure. FIG. 1a shows a perspective front view of the carrier element 10, FIG. 1b shows a perspective plan/top view of the carrier element 10, Figure is shows a perspective side view of the carrier element 10, and FIG. 1d shows a sectional view along line A-A in FIG. 1b (without the markers of FIG. 1b).

As is seen in these figures, the carrier element 10 comprises an outer surface 12 and an inner surface 14. The carrier element 10 further comprises a plurality of markers 16a, 16b that are configured to permit determining a position of the carrier element 10 and thereby also of the tracker, as will be described later. In particular, the carrier element 10 comprises a plurality of passive markers 16a, 16b. The passive markers 16a, 16b include passive flat-shaped markers 16a and passive sphere-shaped markers 16b. The plurality of markers 16a, 16b is provided on the outer surface 12 of the carrier element 10. The passive markers 16a, 16b comprise a reflective surface. The reflective surface may comprise a retroreflective material such as a retroreflective foil. Alternatively, the passive markers 16a, 16b may comprise a glass material.

As is further seen in these figures, the carrier element 10 both extends in a longitudinal direction X and in a direction Y perpendicular to the longitudinal direction, i.e., in a width direction Y. The carrier element 10 has a larger dimension in the longitudinal direction X than in the width direction Y. Furthermore, in the width dimension Y, a maximum width is located in a central portion 18 of the carrier element 10.

In the longitudinal direction X, i.e., along a longitudinal extension, the carrier element 10 has a curved shape. The curved shape is adapted to a curved shape of a base element and a curved shape of a Head-Mounted Display (HMD), as will be explained in more detail later. In essence, this curved shape is substantially defined by the curvature of a person's forehead.

Two or more markers of the plurality of markers 16a, 16b are arranged along the longitudinal extension of the carrier element 10. In particular, the sphere-shaped marker or markers 16b is or are provided in the central portion 18 of the carrier element 10. Specifically, in the present exemplary embodiment, two sphere-shaped markers 16b are provided, which are arranged with a distance in the width direction Y of the carrier element 10. Laterally to the sphere-shaped markers 16b, along a longitudinal extension of the carrier element 10, the flat-shaped passive markers 16a are provided. Specifically, in the present example embodiment, four flat-shaped markers 16a are provided. Two of the four flat-shaped markers 16a are arranged to one side of the sphere-shaped markers 16b, i.e., to the left side with respect to FIGS. 1a to 1d, and the other two of the four flat-shaped markers 16a are arranged to the other side of the sphere-shaped markers 16b, i.e., to the right side with respect to FIGS. 1a to 1d.

The flat-shaped markers 16a are attached to the carrier element 10 so as to be substantially flush with the outer surface 12 of the carrier element 10, and the sphere-shaped markers 16b are attached to the carrier element 10 so as to protrude from the outer surface 12 of the carrier element 10.

The sphere-shaped markers 16b may be configured so as to be individually detachable from the carrier element 10. To this end, the two protrusions 12A protrude from the outer surface 12 on which the sphere-shaped markers 16b can be plugged (see FIG. 1d). The sphere-shaped markers 16b may thus individually be replaced.

Figure 4A:
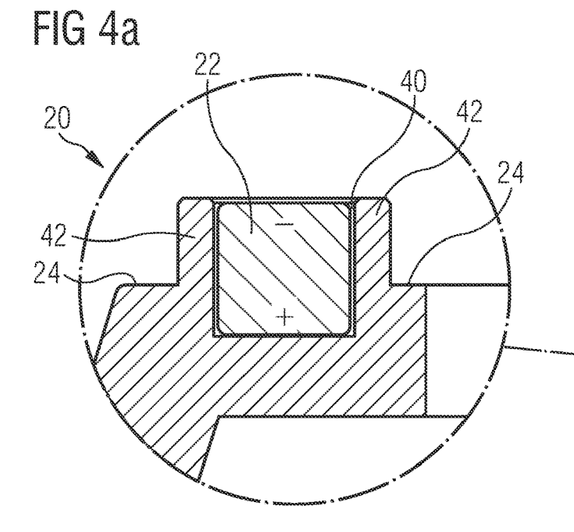
FIGS. 4a-4b schematically show cross-sectional views of the base element of FIGS. 2a-2d.
Figure 4B:
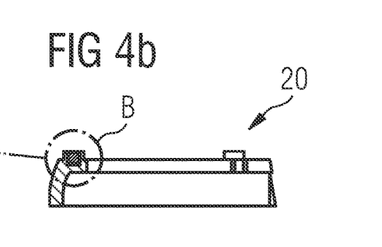

The carrier element 10 is configured to be detachably attachable to an HMD unit so as to realize an HMD that can be tracked. Specifically, the carrier element 10 comprises a structural interface that is configured to detachably plug the carrier element 10 on the HMD unit. A portion of the structural interface can be seen in FIG. 1d of the drawings, and will be explained in more detail with reference to FIG. 4.

Figure 2A:
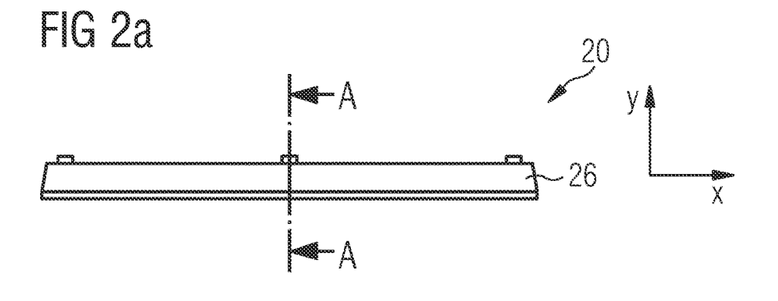
FIGS. 2a-2d schematically show different views of a base element of the tracker.
Figure 2B:
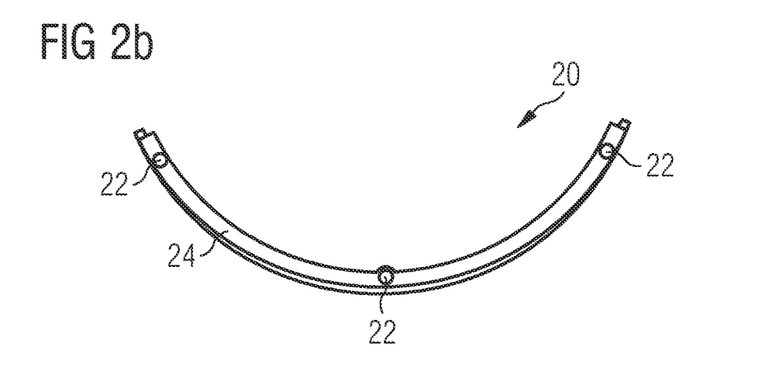
Figure 2C:
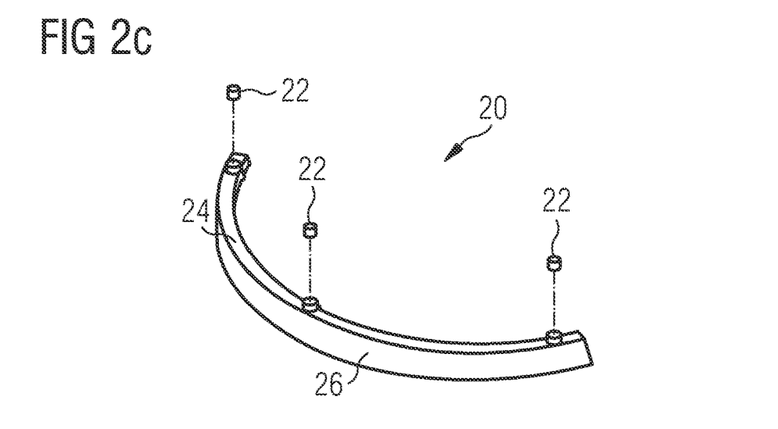
Figure 2D:
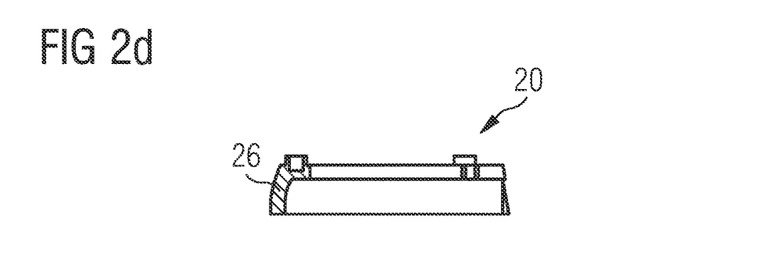

FIGS. 2a to 2d show a base element 20 of a tracker according to an embodiment of the present disclosure. FIG. 2a shows a perspective front view of the base element 20, FIG. 2b shows a perspective plan/top view of the base element 20, FIG. 2c shows a perspective side view of the base element 20, and FIG. 2d shows a sectional view along line A-A in FIG. 2a.

Like the carrier element 10, the base element 20 extends in the longitudinal direction X, i.e., has a longitudinal extension, and has a curved shape along the longitudinal extension. The base element 20 also extends in a direction Y perpendicular to the longitudinal direction, i.e., in a width direction Y. The base element 20 has a larger dimension in the longitudinal direction X than in the width direction Y. Furthermore, an extension of the base element 20 in the width dimension Y is substantially constant in the longitudinal direction.

The curved shape of the base element 20 is adapted to a curved shape of the HMD unit, as will be explained in more detail later. In particular, the base element 20 is configured to be permanently fixed to the HMD unit so as to extend in a circumferential direction of the HMD unit when being fixed to the HMD unit.

The carrier element 10 has a curved shape that corresponds to the curved shape of the base element 20. Specifically, the carrier element 10 is configured to be detachably attachable to the HMD unit by being detachably attachable to the base element 20. Specifically, the carrier element 10 is detachably attachable to the base element 20 by plugging the carrier element 10 on the base element 20. For that purpose, the base element 20 may have a structural interface that is configured to cooperate with the structural interface of the carrier element 10 so as to detachably plug the carrier element 10 on the base element 20.

The structural interface may be configured to detachable attach the carrier element 10 to the base element 20. For that purpose, the structural interface may provide attachment means for detachably attaching the carrier element 10 to the base element 20.

The base element 20 comprises one or more and, in the present embodiment, three magnetic elements 22 that are part of a structural interface cooperating with the carrier element 10. As can be seen in FIGS. 2a to 2c, the magnetic elements 22 are provided on a narrow side surface 24 of the base element 20 along the longitudinal extension of the base element 20. The narrow side surface 24 forms a flat upper surface. The narrow side surface 24 is oriented with an angle in the range of 80° to 100° with respect to a front surface 26 of the base element 20.

As said, in the present embodiment, three magnetic elements 22 are provided. In general, according to the present disclosure, one or more magnetic elements 22 are provided. Furthermore, in the present embodiment, each of the magnetic elements 22 is arranged in a respective opening which is formed on the side surface. In particular, in the present example embodiment, each of the openings is formed in a respective projection formed on the narrow side surface 24, as will be explained later with respect to FIGS. 4a and 4b.

The magnetic elements 22 of the base element 20 are arranged and configured to cooperate with one or more magnetic elements of the carrier element 10. In particular, the carrier element of FIGS. 1a to 1d comprises three magnetic elements which are arranged at respective positions, as will be described below in more detail with reference to FIGS. 4 and 5 of the drawings.

Figure 3A:
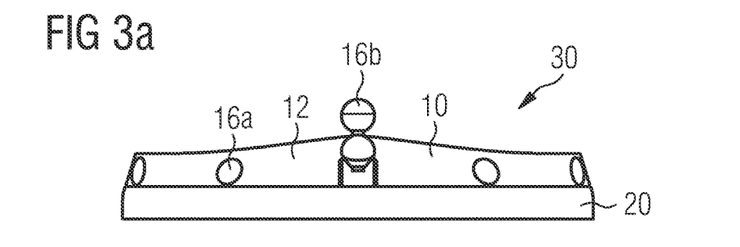
FIGS. 3a-3d schematically show different views of the tracker comprising the carrier element of FIGS. 1a-1d and the base element of FIGS. 2a-2d.
Figure 3B:
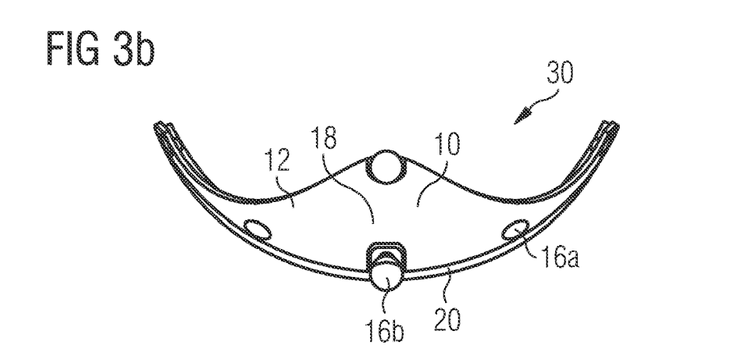
Figure 3C:
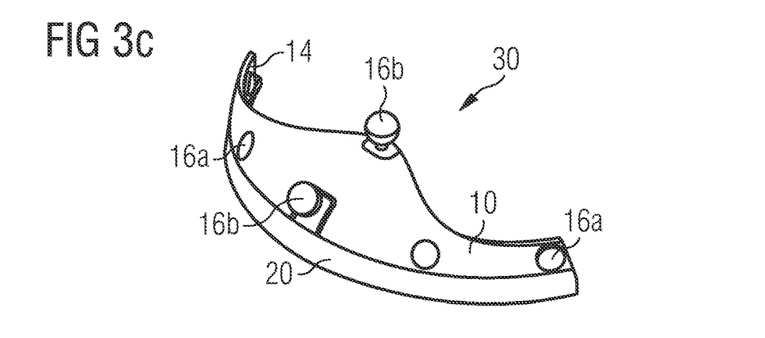
Figure 3D:
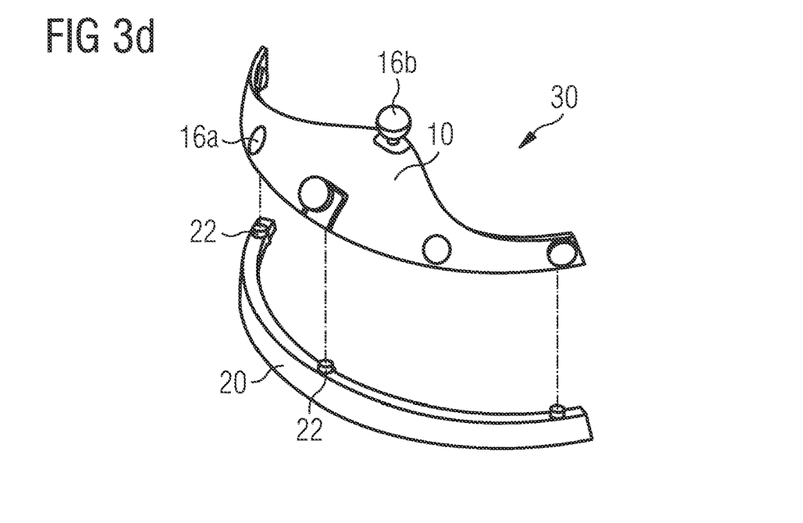

FIGS. 3a to 3d show a tracker 30 comprising the carrier element 10 detachably attached to the base element 20. FIG. 3a shows a perspective front view of the tracker 30, FIG. 3b shows a perspective plan/top view of the tracker 30, FIG. 3c shows a perspective side view of the tracker 30, and FIG. 3d shows a perspective side view of each of the carrier element 10 and the base element 20, oriented to each other and shortly before the carrier element 10 is plugged on the base element 20.

As can be seen in these FIGS. 3a to 3d, in an attached state of the base element 20 and the carrier element 10, the narrow side surfaces 24, 34 of the base element 20 and carrier element 10, respectively, abut against each other so that the magnetic elements 22 come into contact with each other (or at least come into close proximity so as to result in a sufficiently attractive force). The carrier element 10 is plugged on the base element 20, in particular on an upper side surface with respect to FIGS. 3a to 3d, i.e., the narrow side surface 24, of the base element 20. Thus, the outer surface 12 of the carrier element 10 is extended by the front surface 26 of the base element 20 in the width direction Y. In particular, the outer surface 12 of the carrier element 10 is angled with respect to the front surface 26 of the base element 20.

As can be further seen, the curved shape along the longitudinal extension of the carrier element 10 corresponds to the curved shape along the longitudinal extension of the base element 20, at least at an interface region of the carrier element 10 and the base element 20. In other words, the base element 20 and the carrier element 10 substantially comprise the same radius of curvature where the base element 20 and the carrier element 10 contact each other. Furthermore, a length of the carrier element 10 in the longitudinal direction X substantially corresponds to a length of the base element 20 in the longitudinal direction X. Thus, as is seen in FIGS. 3a and 3c, the carrier element 10 and the base element 20 end flush in a longitudinal direction X.

FIGS. 4a and 4b show cross-sectional views through a portion of the base element 20 where a opening 40 for receiving a magnetic element 22 is provided, i.e., for example along line A-A of FIG. 2a. FIG. 4b corresponds to FIG. 2d, wherein, in FIG. 4b, a magnetic element 22 is shown to be placed into the opening 40. FIG. 4a shows an enlarged view of section B in FIG. 4b.

In the embodiment of FIGS. 4a and 4b, the magnetic element 22 is arranged in a respective opening 40 which is formed on the narrow side surface 24 of the base element 20. In particular, in the present embodiment, the opening 40 is at least partly formed in a respective projection 42 formed on the narrow side surface 24. The projection 42 projects from the narrow side surface 24 of the base element 20. The projection 42 is configured to matingly cooperate with a respective recess 44 formed in the carrier element 10. For each of the magnetic elements 22, a respective opening 40 at least partly formed in a respective projection 42 formed on the narrow side surface 24 is provided.

Figure 5A:
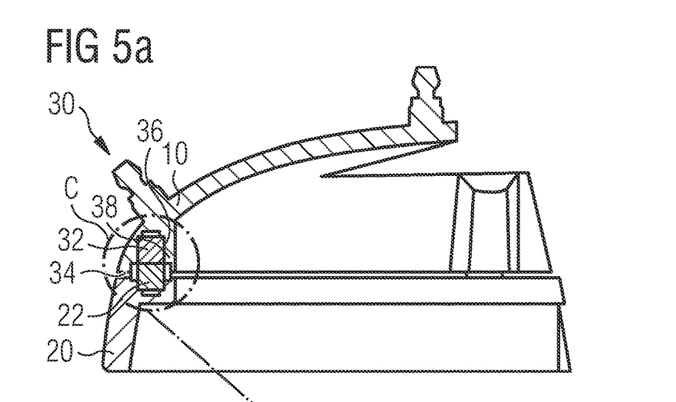
FIGS. 5a-5b schematically show cross-sectional views of a carrier element attached to the base element as shown in FIGS. 3a-3d.
Figure 5B:
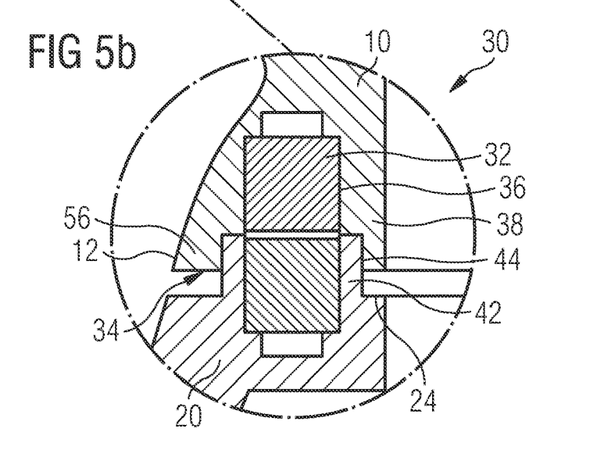

The cooperation between a projection 42 and a recess 44 is shown in FIGS. 5a and 5b. FIG. 5a shows a cross-section through a tracker 30 as is illustrated in FIGS. 3a to 3d, at a portion of the system where the magnetic elements 22, 32 cooperate with each other. FIG. 5b shows an enlarged view of section C in FIG. 5a.

Each of the magnetic elements 32 is arranged along a narrow side surface 34 of the carrier element 10, wherein the narrow side surface 34 connects the inner surface 14 with the outer surface 12 of the carrier element 10. Like the base element 20, the carrier element 10 comprises openings 36 for receiving the magnetic elements 32. The openings 36 are formed in the narrow side surface 34. In the embodiment of FIGS. 1a to 1d, the openings 36 are provided in regions of the carrier element 10 where the narrow side surface 34 has an extended cross section. The extended cross-section is formed by bulges 38 on the inner surface 14 of the carrier element 10.

As is seen in FIG. 5b, the projection 42 of the base element 20 is sized so as to be received by a respective recess 44 in the carrier element 10. By being received by the recess 44, the carrier element 10 and the base element 20 are positionally aligned with each other. Thus, the recess 44 and the respective projection 42 provide complementary form-fitting alignment elements. Hence, when plugging the carrier element 10 on the base element 20, the alignment elements 42, 44 cooperate so with each other that the carrier element 10 and the base element 20 are precisely positioned with respect to each other, thereby ensuring that the markers 16a, 16b can be replaced with positional accuracy when replacing the carrier element 10.

When the carrier element 10 and the base element 20 are positionally aligned with each other due to the alignment elements 42, 44, the interfaces of the carrier element 10 and the base element 20 cooperate with each other. In particular, the interfaces are structurally configured to attach the carrier element 10 to the base element 20. In the present example embodiment, the magnetic element 32 of the carrier element 10 and the magnetic element 22 of the base element 20 are configured and arranged so as to provide a detachable attachment of the carrier element 10 to the base element 20.

The magnetic element 32 of the carrier element 10 is arranged in the opening 36 formed in the carrier element 10. The opening 36 adjoins the recess 44 and has a smaller width dimension than the recess 44. Analogously, the magnetic element 22 of the base element 20 is arranged in the opening 40 formed in the projection 42. Consequently, the width dimension of the opening 40 of the base element 20 is smaller than an outer diameter of the projection 42 and substantially corresponds to the width dimension of the opening 36 of the carrier element 10. Furthermore, the magnetic elements 22, 32 of the carrier element 10 and the base element 20, respectively, opposing each other are so arranged that an attractive force is exerted upon approaching the magnetic elements 22, 32.

As is described above with reference to FIGS. 1 and 2, each of the base element 20 and the carrier element 10 may generally comprise one and more magnetic elements 22, 32 configured to cooperate with each other. Thus, in case of more than one magnetic element 22, 32 for each of the carrier element 10 and base element 20, for example in the case of three magnetic elements 22, 32 for each of the carrier element 10 and the base element 20 as is illustrated in FIGS. 1 and 2, each of the cooperating magnetic elements 22, 32 is arranged and configured as described with reference to FIGS. 5a and 5b of the drawings. Thus, for each of the magnetic element pairs 22, 32, a corresponding opening 36, 40 is formed in the carrier element 10 and in the base element 20 in respective opposite portions of the carrier element 10 and the base element 20.

Correspondingly, for each of the magnetic element pairs 22, 32, an alignment structure is formed positionally aligning the carrier element 10 with the base element 20. In particular, for each of the magnetic element pairs 22, 32, a recess 44 and a correspondingly shaped and dimensioned projection 42 is formed forming a form-fitting alignment structure.

Instead of forming the projection 42 in the base element 20 and the recess 44 in the carrier element 10, it is also possible to form a recess in the base element 20 and a correspondingly shaped and dimensioned projection in the carrier element 10, or to use any other matingly configured geometric structures. The recess 44 and the projection 42 constitute a kind of bolt-and-groove configuration for positionally aligning the carrier element 10 and the base element 20. According to the present disclosure, also any other kind of alignment elements may be provided, such as, for example, alignment surfaces and/or alignment pins.

FIGS. 6a to 6e schematically show an example of verification elements for verifying that the carrier element 10 and the base element 20 are positionally aligned with respect to each other.

Figure 6A:
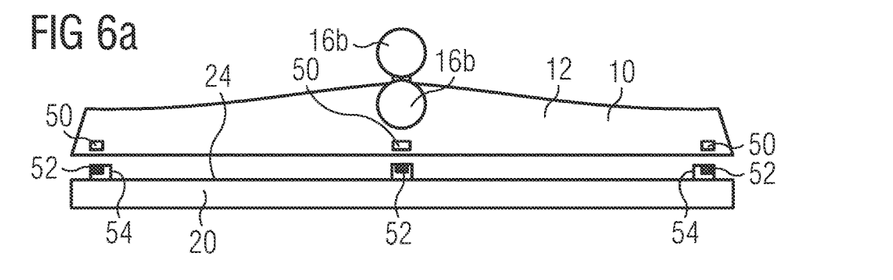
FIGS. 6a-6e schematically show an embodiment of a tracker with a base element and a carrier element comprising verification elements.
Figure 6B:
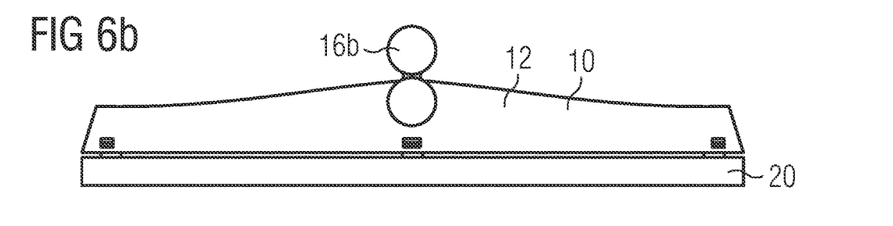
Figure 6C:
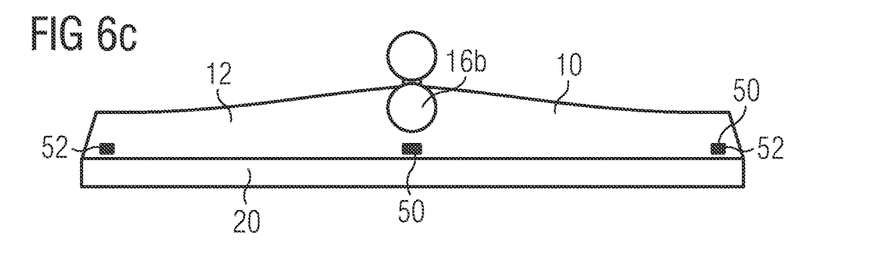
Figure 6D:
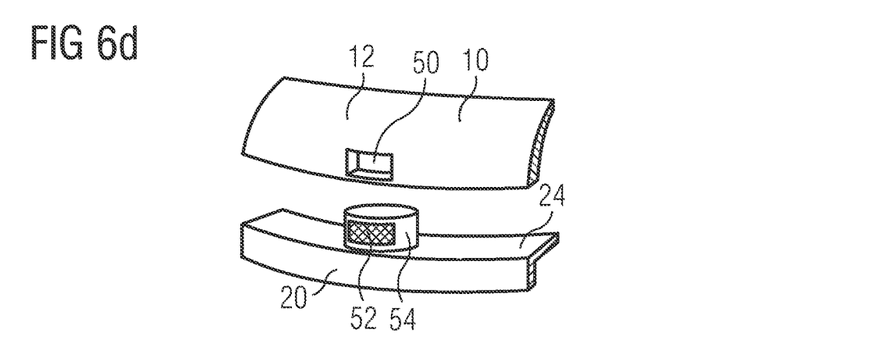
Figure 6E:
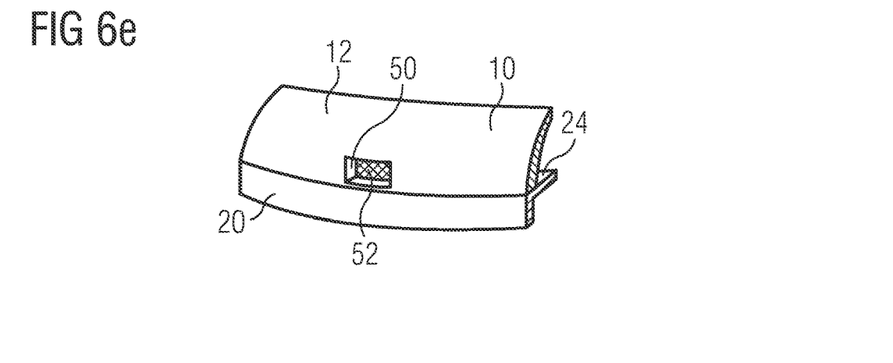

In particular, FIG. 6a shows the carrier element 10 and the base element 20 in a state separated from each other, FIG. 6c shows a state in which the carrier element 10 is attached to the base element 20, and FIG. 6b shows the carrier element 10 and the base element 20 being closely arranged to each other short before being attached to each other. FIG. 6d and FIG. 6e show an enlarged view of portions of the carrier element 10 and the base element 20 comprising the verification elements of FIGS. 6a and 6c, respectively.

The carrier element 10 comprises a window 50 which is arranged and sized so as to coincide with a marking 52 provided on the base element 20 when the base element 20 and the carrier element 10 are positionally aligned with respect to each other. In the present example embodiment, the base element 20 comprises a protruding feature 54 such as a projection which protrudes from the narrow side surface 24 of the base element 20. The protruding feature 54 comprises the marking 52. The window 50 is provided on the outer surface 12 of the carrier element 10. If the carrier element 10 and the base element 20 are positionally aligned with each other, the window 50 overlaps the protruding feature 54 so that the marking on the protruding feature 54 can be seen through the window 50. The window 50 and the marking 52 have the function of verification elements which are configured and arranged for enabling a user to verify that the carrier element 10 and the base element 20 are orientated with respect to each other in an intended manner.

In the present example embodiment, three windows 50 are provided at the carrier element 10 which cooperate with three markings 52 provided at the base element 20, respectively. However, the carrier element 10 and the base element 20 may comprise any other number of verification elements, such as one verification element, two verification elements, four verification elements, or five verification elements, for example.

The window 50 may be configured as a through-hole provided in the carrier element 10 or may be configured as a transparent or at least partly transparent area of the carrier element 10. The marking 52 may be any kind of pattern or information, such as a geometrical pattern, text information or picture information, for example.

When looking at FIG. 5b of the drawings, the marking 52 may be provided at a projection 42 of the base element 20 cooperating with a corresponding recess 44 provided in the carrier element 10 provided for positionally aligning the base element 20 and the carrier element 10 with respect to each other. In that case, the window 50 is provided at a portion of a front wall 56 of the carrier element 10 (cf. FIG. 5b) delimiting the recess 44 to a front side of the carrier element 10.

In the alternative, additional protruding features 54 to the alignment projection 42 may be provided at the base element 20 for carrying the markings 52.

Figure 7A:
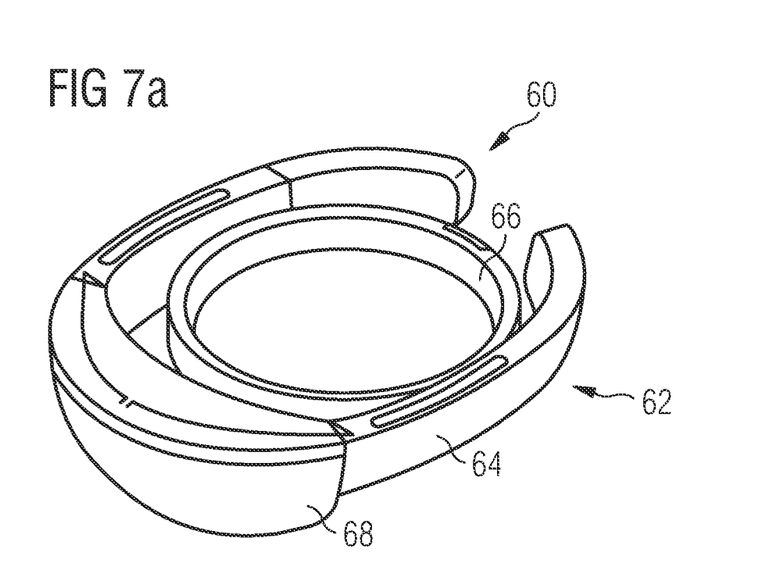
FIGS. 7a-7d schematically show perspective views of a HMD with a HMD unit, in FIG. 7a without a tracker attached thereto and in FIGS. 7b-7d with a tracker attached thereto.
Figure 7B:
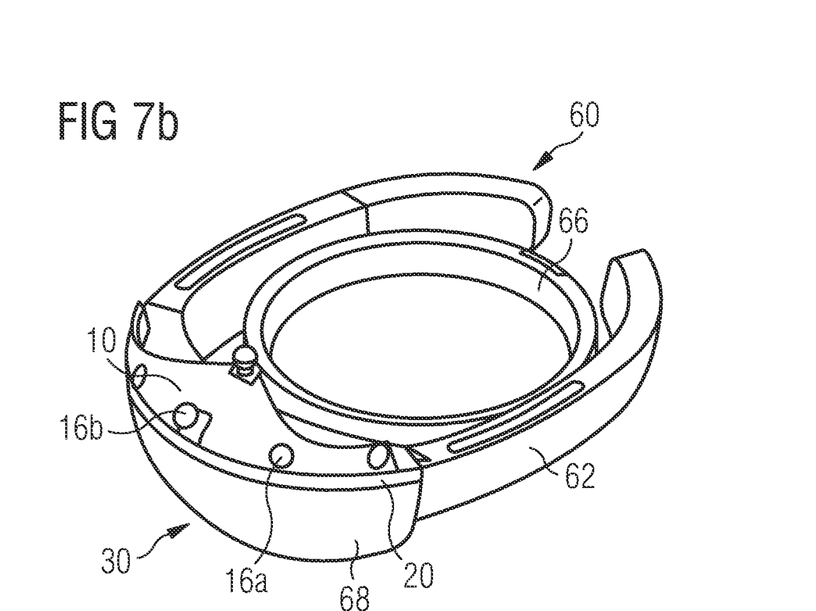
Figure 7C:
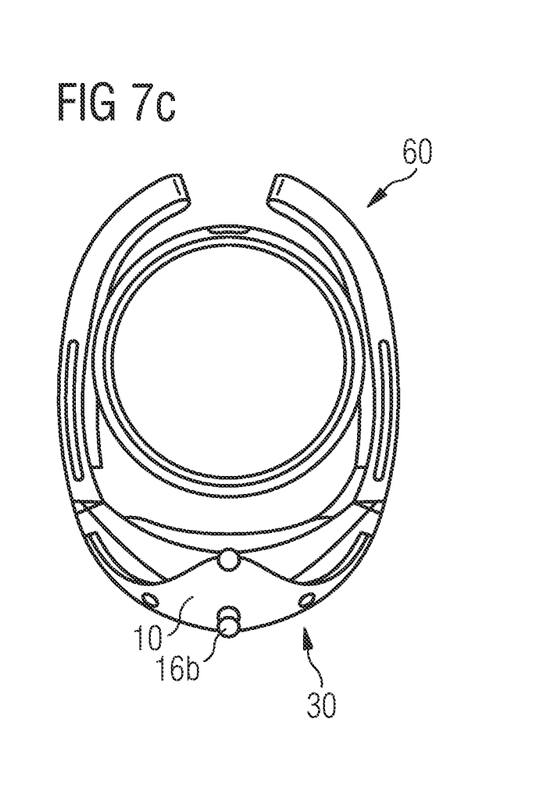
Figure 7D:
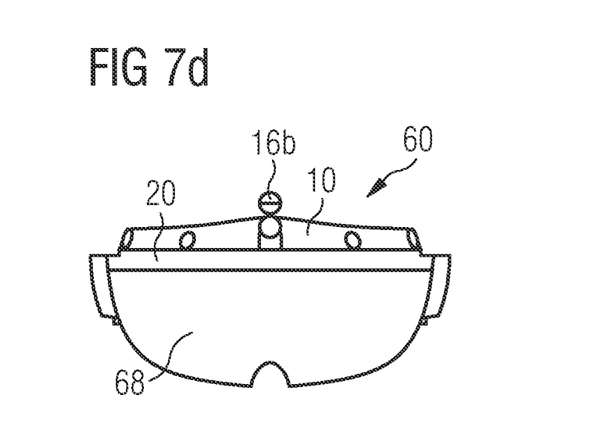

FIGS. 7a to 7d show an HMD 60 for a navigation system which comprises a HMD unit 62 and a tracker 30 as described above. FIG. 7a shows a perspective side view of the HMD unit 62 without the tracker 30 mounted thereto, FIG. 7b shows a perspective side view of the HMD 60 with the tracker 30 mounted thereto, FIG. 7c shows a perspective top view of the HMD 60, and FIG. 7d shows a perspective front view of the HMD 60.

The HMD unit 62 of FIG. 7a comprises a head-mountable structure 64 which comprises an adjustable headband 66 to hold the HMD 60 on a user's head. The HMD unit 62 is configured as or to accommodate a display such as a HoloLens® by Microsoft Corporation capable of displaying virtual information to appear at desired coordinates in a desired coordinate system. The information and/or images are overlaid onto the real world so as to appear to be located in the real world environment at desired coordinates in the real world environment. The HMD unit 62 further comprises a visor 68.

The displayed virtual information may be, for example, patient image data, planning objects such as anatomic objects, trajectories, points, lines, implants etc., alignment information, tool information, text notes, picture notes, video windows, status information etc. The displayed virtual information may be overlaid on real world environment such as the real patient anatomy seen through the HMD unit.

FIGS. 7b to 7d show the tracker 30 attached to the HMD unit 62. As can be seen, the tracker 30 is attached to a front side of the HMD unit 62. In particular, the base element 20 of the tracker 30 is fixedly attached to the HMD unit 62, more particular, to an upper rim to of the HMD unit 62, for example by adhesive bonding. Generally, according to the present disclosure, the base element 20 may also be detachably attached to the HMD unit 62.

The carrier element 10 has been plugged on the base element 20 so as to be detachably attached to the base element 20 and, thus, to the HMD unit 62. In particular, the carrier element 10 is positionally aligned with respect to the base element 20 so that the projections 42 of the base element 20 are received by the respective recesses 44 of the carrier element 10, respectively, as has been described with reference to FIGS. 5a and 5b above. In that position, the magnetic elements 32, 22 of the carrier element 10 and the base element 20 face each other. Since the magnetic elements 32, 22 in the openings 36, 40 are arranged so that a negative pole of the one magnetic element 32, 22 faces a positive pole of the other magnetic element 22, 32, or vice versa, there is an attractive force between the carrier element 10 and the base element 20 by means of which the carrier element 10 is detachably attached to the base element 20 and, thus, to the HMD unit 62.

In the attached state, the markers 16a, 16b carried by the carrier element 10 are located in a front upper part of the HMD 60 above the visor 68, i.e., above a user's field of view. When worn by a user, the markers 16a, 16b partly surround the user's head and are located above or in an upper region of the user's head. In the central portion 18 of the carrier element 10, the carrier element 10 is shaped so as to extend towards the back of the HMD 60, that means, the carrier element 10 has a greater width dimension in the central portion 18 than in side regions of the carrier element 10. In the central portion 18, the two sphere-shaped markers 16b are disposed adjacent to each other so as to be arranged one above the other. Laterally to the sphere-shaped markers 16b, along the longitudinal extension of the carrier element 10, the flat-shaped markers 16a are arranged. The flat-shaped markers 16a do not obstruct the "field-of view" of the sphere-shaped markers 16b.

The HMD 60 may thus be part of a surgical navigation system, which further comprises an optical sensor capable of detecting light reflected by the two or more markers 16a, 16b and of generating a sensor signal indicative of the detected light. The surgical navigation system may further comprise a navigation controller capable of receiving the sensor signal and determining at least one of a position and/or an orientation of the tracker 30 in a coordinate system of the surgical navigation system. In that way, the position and/or orientation of the tracker 30 and thus of the HMD 60 can be determined in a coordinate system of the surgical navigation system.

According to the present disclosure, the markers 16a, 16b may be simply replaced by replacing the carrier element 10 of the tracker 30 comprising the markers 16a, 16b. Thus, the carrier element 10 may be a disposable item. Since the markers 16a, 16b do not have to be replaced individually, the markers 16a, 16b may be replaced in a time-effective manner.

Furthermore, due to the attachment by the clip-on mechanism comprising, for example, the magnetic elements 22, 32, the carrier element 10 can be replaced easily without damaging the HMD unit 62. In addition, since there are no structures provided for individually replacing the flat-shaped markers 16a, such as, for example, screws and/or sockets, the tracker 30 may be configured in a light-weight manner. The clip-on mechanism provides a secure and simple attachment solution.

By way of the alignment elements 42, 44, it is allowed to replace the carrier element 10 with reproducible positional accuracy, thereby ensuring that the markers 16a, 16b have the same positional orientation with respect to the HMD unit 62 before and after a replacement cycle.

By way of the verification elements 50, 52, the correct alignment between the carrier element 10 and the base element 20 and/or HMD unit 62 may be confirmed in a simple and reliable manner.

Since the markers 16a, 16b may at least include one or more passive flat-shaped markers 16a and one or more passive sphere-shaped markers 16b, the characteristics and advantages of both marker types may be combined. Specifically, the sphere-shaped markers 16b have the advantage that they can see light that is incident from all directions, whereas the flat-shaped markers 16a only see light under incident angles of typically up to about 45°. However, flat-shaped markers are, compared to sphere-shaped markers, more cost-effective, easier to clean and simpler to produce. Furthermore, flat-shaped markers which are arranged adjacent to each other do not cover each other, i.e., they do not obstruct the field of view of an adjacent marker.

Correspondingly, when the one or more sphere-shaped markers 16b are arranged in the central portion 18 of the carrier element 10 with respect to a longitudinal extension of the carrier element 10 and the one or more flat-shaped markers 16a are arranged laterally to the one or more sphere-shaped markers 16b, the centrally arranged sphere-shaped marker 16b or markers 16b may reflect incoming light from both lateral sides and from the front, and the laterally arranged flat-shaped markers 16a may also reflect incoming light from one side and from the front, without covering the sphere-shaped marker 16b or markers 16b.

By way of the markers 16a, 16b, the position of the HMD 60 with respect to the surgical navigation system can be determined, so that the virtual information may be displayed relative to the HMD 60. In that way, relevant information such as trajectories for guiding the tool may be displayed positionally accurately with respect to the surgical region seen through the HMD 60 by the surgeon.

In particular, in the present example, more than two markers 16a, 16b are provided on the tracker 30. In that case, the position and orientation of the tracker 30 can be determined accurately and reliably by the navigation system. Generally, in the present disclosure, also only one marker 16a, 16b or only two markers 16a, 16b may be provided on the tracker 30. In that case, the determination of the position and orientation of the tracker 30 requires another source of information such as an inertial measurement unit (IMU) or a tracking system of the HMD. Such other information can then be synchronized using several measurements over time.

In the following, further aspects of a tracker and a HMD according to embodiments of the present disclosure are described. Some of these aspects have already been discussed above with reference to the figures.

(Aspect 1) A tracker for a Head-Mounted Display, HMD, unit, the tracker comprising
    a carrier element carrying one or more markers that are configured to permit determining a position of the tracker, the carrier element being configured to be detachably attachable to the HMD unit,
    wherein the two or more of the markers are arranged along a longitudinal extension of the carrier element, and wherein the carrier element has a curved shape in its longitudinal extension.

(Aspect 2) The tracker of aspect 1, wherein
    the carrier element comprises a structural interface that is configured to detachably plug the carrier element on the HMD unit.

(Aspect 3) The tracker of aspect 1 or 2, wherein
    the carrier element comprises at least one magnetic element configured to cooperate with a magnetic element provided on the HMD unit for detachably attaching the carrier element to the HMD unit.

(Aspect 4) The tracker of any of the preceding aspects, wherein the carrier element has an alignment element configured to cooperate with a corresponding alignment element provided on the HMD unit.

(Aspect 5) The tracker of any of the preceding aspects, further comprising
    a base element configured to be fixed to the HMD unit so as to extend in a circumferential direction of the HMD unit when being fixed to the HMD unit, and
    wherein the carrier element is configured to be detachably attachable to the HMD by being detachably attachable to the base element.

(Aspect 6) The tracker of aspect 5, wherein
    the carrier element is detachably attachable to the base element by plugging the carrier element on the base element.

(Aspect 7) The tracker of aspect 5 or 6, wherein
    the carrier element and the base element each comprise a magnetic element for detachably attaching the carrier element to the base element.

(Aspect 8) The tracker of any of aspects 5 to 7, wherein
    the carrier element and the base element each comprise an alignment element configured to cooperate with each other so as to positionally align the carrier element with the base element.

(Aspect 9) The tracker of aspect 8, wherein
    the base element and the carrier element comprise complementary form-fitting alignment elements.

(Aspect 10) The tracker of any of aspects 5 to 9, wherein
    the base element is configured for being permanently fixed to the HMD unit.

(Aspect 11) The tracker of any of the preceding aspects, wherein
    two or more markers are provided which include:
        one or more passive flat-shaped markers; and
        one or more passive sphere-shaped markers.

(Aspect 12) The tracker according to aspect 11, wherein
    the one or more sphere-shaped markers are arranged in a central region of the carrier element with respect to its longitudinal extension and the one or more flat-shaped markers are arranged laterally to the one or more sphere-shaped markers.

(Aspect 13) The tracker according to any of the preceding aspects, wherein
the tracker comprises one or more verification elements configured to permit verifying that the carrier element and the HMD unit are positionally aligned with each other.

(Aspect 14) The tracker according to aspect 13, when depending on any of aspects 5 to 10, wherein the one or more verification elements comprises at least one of
markings provided on the carrier element and the base element so as to align with each other when the base element and the carrier element are positionally aligned;
a gap which is formed between the base element and the carrier element, wherein the size of the gap is constant over the whole length of the gap when the base element and the carrier element are positionally aligned; and
a window provided on the carrier element so as to align with a marking on the base element when the base element and the carrier element are positionally aligned.

(Aspect 15) A Head-Mounted Display, HMD, for a navigation system, comprising
an HMD unit and a tracker according to any of the preceding aspects.

While the present disclosure has been described with reference to exemplary embodiments, it will be appreciated that the present disclosure can be modified in many ways without departing from the scope of the invention as defined by the appended claims.

The invention claimed is:

1. A tracker for a Head-Mounted Display ("HMD") unit, the tracker comprising
a carrier element carrying one or more markers that are configured to permit determining a position of the tracker, the carrier element being configured to be detachably attachable to the HMD unit; and
a base element configured to be fixed to the HMD unit so as to extend in a circumferential direction of the HMD unit when being fixed to the HMD unit,
wherein the carrier element comprises at least one magnetic element configured to cooperate with at least one magnetic element provided on the base element to be fixed to the HMD unit, for detachably attaching the carrier element to the HMD unit.

2. The tracker of claim 1, wherein
two or more markers are provided, wherein at least some of the two or more markers are arranged along a longitudinal extension of the carrier element, and
wherein the carrier element has a curved shape in its longitudinal extension.

3. The tracker of claim 1, wherein
the carrier element has an alignment element configured to cooperate with a corresponding alignment element provided on the HMD unit or on the base element to be fixed to the HMD unit.

4. The tracker of claim 1, wherein
the carrier element and the base element each comprise an alignment element configured to cooperate with each other so as to positionally align the carrier element with the base element.

5. The tracker of claim 1, wherein
the base element and the carrier element comprise complementary form-fitting alignment elements.

6. The tracker of claim 1, wherein
the base element is configured for being permanently fixed to the HMD unit.

7. The tracker of claim 1, wherein
two or more markers are provided which include:
one or more passive flat-shaped markers; and
one or more passive sphere-shaped markers.

8. The tracker of claim 7, wherein
the one or more sphere-shaped markers are arranged in a central portion of the carrier element with respect to its longitudinal extension and the one or more flat-shaped markers are arranged laterally to the one or more sphere-shaped markers.

9. The tracker of claim 1, wherein
the tracker comprises one or more verification elements configured to permit verifying that the carrier element and the HMD unit are positionally aligned with each other.

10. The tracker of claim 9, further comprising
the base element configured to be fixed to the HMD unit so as to extend in a circumferential direction of the HMD unit when being fixed to the HMD unit, and
wherein the carrier element and the base element each comprise the respective at least one magnetic element and wherein the one or more verification elements comprise at least one of:
one or more markings provided on the carrier element and the base element so as to align with each other when the base element and the carrier element are positionally aligned;
a gap which is formed between the base element and the carrier element, wherein the size of the gap is constant over the whole length of the gap when the base element and the carrier element are positionally aligned; and
a window provided on the carrier element so as to align with a marking on the base element when the base element and the carrier element are positionally aligned.

11. A tracker for a Head-Mounted Display ("HMD") unit, the tracker comprising:
a carrier element carrying one or more markers that are configured to permit determining a position of the tracker, the carrier element being configured to be detachably attachable to the HMD unit;
wherein the carrier element comprises at least one magnetic element configured to cooperate with at least one magnetic element provided on the HMD unit or on a base element to be fixed to the HMD unit, for detachably attaching the carrier element to the HMD unit, and
wherein the tracker comprises one or more verification elements configured to permit verifying that the carrier element and the HMD unit are positionally aligned with each other.

12. A tracker for a Head-Mounted Display ("HMD") unit, the tracker comprising:
a carrier element carrying one or more markers that are configured to permit determining a position of the tracker, the carrier element being configured to be detachably attachable to the HMD unit;
wherein the carrier element comprises at least one magnetic element configured to cooperate with at least one magnetic element provided on the HMD unit or on a base element to be fixed to the HMD unit, for detachably attaching the carrier element to the HMD unit, and
wherein two or more markers are provided which include one or more passive flat-shaped markers and one or more passive sphere-shaped markers, wherein the one or more sphere-shaped markers are arranged in a central portion of the carrier element with respect to its longitudinal extension and the one or more flat-shaped markers are arranged laterally to the one or more sphere-shaped markers such that the centrally arranged sphere-shaped markers may reflect incoming light from both sides and a front, and the laterally arranged flat-shaped marker or markers may also reflect incoming light from one of the sides and the front.

* * * * *